United States Patent [19]

Apap et al.

[11] Patent Number: 4,940,410
[45] Date of Patent: Jul. 10, 1990

[54] DENTAL TOOL HOLDER

[75] Inventors: Marc F. C. Apap, Montrouge; Cedric L. M. C. Thorin, Paris, both of France; Otto Rosenstatter, Seeham; Peter Malata, Bürmoos, both of Austria

[73] Assignee: Dentalwerk Bürmoos Gesellschaft m.b.H., Bürmoos, Austria

[21] Appl. No.: 235,649

[22] Filed: Aug. 24, 1988

[30] Foreign Application Priority Data

Aug. 24, 1987 [AT] Austria ............................ 2108/87

[51] Int. Cl.⁵ ............................................. A61C 5/02
[52] U.S. Cl. ................................. 433/102; 433/116; 433/127; 433/128
[58] Field of Search ............... 433/102, 116, 127, 128, 433/225, 81

[56] References Cited

U.S. PATENT DOCUMENTS

| | | |
|---|---|---|
| 2,010,210 | 8/1935 | Witt ........................ 433/128 |
| 2,338,437 | 1/1944 | Karl ........................ 433/128 |
| 3,967,380 | 7/1976 | Malata et al. ............ 433/128 |
| 4,219,620 | 8/1980 | Carse ...................... 433/225 |
| 4,330,278 | 5/1982 | Martin ..................... 433/81 |
| 4,571,183 | 2/1986 | Nash ....................... 433/127 |
| 4,778,387 | 10/1988 | Komatsu ................ 433/116 |

FOREIGN PATENT DOCUMENTS 0191574 8/1986 European Pat. Off. ............ 433/102

*Primary Examiner*—John J. Wilson
*Attorney, Agent, or Firm*—Toren, McGeady & Associates

[57] ABSTRACT

A dental toolholder (2) has an endodontic filing tool (18) which is clamped in the toolholder so as to be secured against rotational and axial movements. A vibrating movement is impressed on the tool. The tool (18) can be clamped at its rear shaft end with a slight play and the vibrations can be imparted to the tool at its front shaft end (15). This part encloses the front shaft end (7b) with slight play and comprises a cylindrical recess whose cross-sectional shape has a constant-diameter configuration. Accordingly, the tool is set into a swinging movement perpendicular to its axis. The structural component part (15) rotates preferably at approximately 20,0000 rpm.

10 Claims, 3 Drawing Sheets

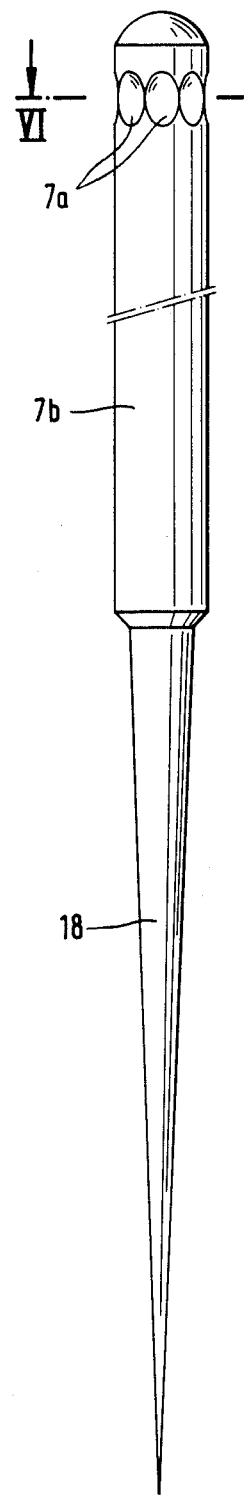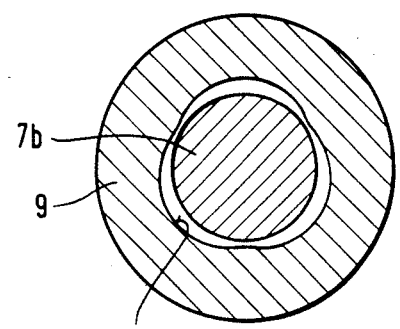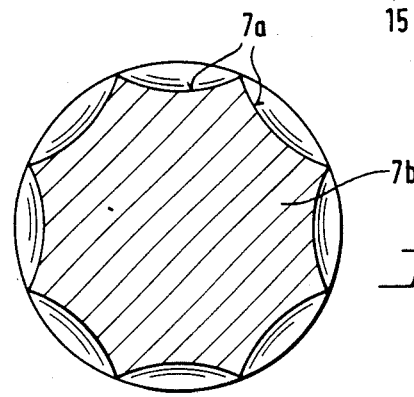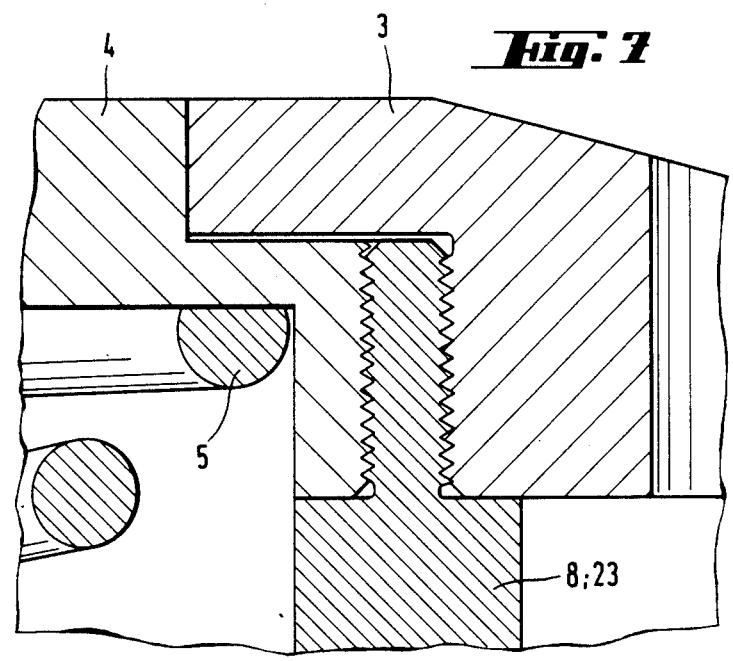

DENTAL TOOL HOLDER

FIELD AND BACKGROUND OF THE INVENTION

The invention is directed to a dental tool holder or handpiece for an endodontic file or filing worktool which is clamped in the tool holder so as to be secured against rotational and axial movements. A vibrating movement is impressed on the worktool.

Such root canal files are known from U.S. Pat. No. 4,571,183 and German OS No. 33 37 367. The file, according to the U.S. patent, executes a combined vibration transversely and longitudinally relative to the file axis, which is particularly important. The oscillations or vibrations in the device according to the German OS are produced according to U.S. Pat. No. 4,330,278 or French Pat. No. 2,505,172 and are completely undefined, but noticeable longitudinal oscillations of the worktool always occur because of the geometry of the tool holder.

In addition to such filing tools, devices are known which work by means of oscillating rotational movement where an axial, swinging lifting movement can also be superimposed on this oscillating rotational movement. The amplitude of this movement is larger by several orders of magnitude than in the above-mentioned files. Because of the inherent rigidity of the filing tool, not all wall areas are reached in curved root canals, and, accordingly, cleaning can be carried out only insufficiently. When the thin filing tool is jammed in the canal, it can be twisted by means of oscillating rotational movement. In devices with swinging lifting movement, there is the additional risk that the base of the root canal will be pushed through and the tooth will be lost.

In filing tools of the type first mentioned, these disadvantages occur only to a limited extent. Until now, such worktools were excited with frequencies between 3 kHz and 20 kHZ, that is, with high frequencies.

Accordingly, there is a disadvantage that the filing tool is easily overloaded and broken. Also, despite the high frequency applied to the filing tool, the amplitude of the oscillations observably decreases as the distance from the worktool holder increases when it is introduced into the root canal, i.e., only an insufficient cleaning effect is achieved in the lower area of the root canal. Moreover, there is the risk that the worktool will dig into the dentin and thus will drill its own, false canal.

The nerve canals in the human tooth have divergent anatomical forms. They are circular to sharply oval in cross section and straight to sharply curved in longitudinal forms. They have a varying quantity of outlets in the apex area, various lengths in the canal and sharp reductions in cross section in the apex area.

SUMMARY OF THE INVENTION

The object of the invention is to provide a dental tool holder for an endodontic filing tool in which the shaft of the worktool is held so as to be secured against rotational and axial movements, wherein an exciter device is provided in the tool holder which sets the worktool in a motion comprising a component which is transverse relative to the axis of the worktool, which dental tool does not have the aforementioned disadvantages and is suitable for all root canal shapes.

According to the invention, the worktool is held at its rear shaft end with a slight play and projects through a cylindrical borehole with its front shaft end, the cylindrical borehole having a cross section of constant diameter or a polygonal cross section, wherein the borehole is arranged in a structural component part which is supported in the tool holder head so as to be rotatable as an exciter device which is drivable in a known manner, e.g., by means of an angular drive.

The amplitude of the vibration which is transmitted in this way also hardly decreases in the root canal in the direction toward the end of the worktool and, accordingly, enables better cleaning than was possible until now. Moreover, the risk of the file breaking or of its digging its own canal in the dentin is reduced to an extraordinary degree.

During operation, the exciter structural component part preferably revolves at approximately 20,000 rpm. Accordingly, a swinging frequency of approximately 1 kHz results, which has proven to be substantially more sure relative to the known devices with high-frequency drive.

According to the present invention, a surprising result is achieved in that a cooling and cleaning fluid which is used in conjunction with the tool holder, and which exits close to the filing tool in a jet which is directed toward the filing tool, envelops the tool and runs down along its length to the end of the tool, thereby effectively carrying away residue which would otherwise accumulate and the ever-widening root canal being opened by the filing tool.

As noted above, in medical applications, the tip of the filing tool must not penetrate the apex of the tooth, but must reach the height of the apex in a sure manner so that the entire canal can be cleaned, widened and completely filled subsequently. To this end, the invention includes an adjustable depth stop which can reduce the available working length of the filing tool, preferably by up to 9 mm.

Since most conventional filing tools have overall working lengths of 21, 25 and 28 mm, nerve canals with depths of 12 to 28 mm can be treated with a depth stop which is adjustable from 0 to 9 mm. This is sufficient for the overwhelming number of occurring treatments. Of course, an additional depth stop can be provided in special cases.

A difficulty in the treatment of root canals consists in the frequent changing of tools, wherein it is necessary to insert the filing tool, which is small and difficult to handle, in the holder system of the angular tool holder in the correct angular position.

For this reason, in a construction of the invention, a plurality of hemispherical recesses are provided at the shaft of the file which are uniformly distributed around the circumference of the shaft and which cooperate with clamping balls of a clamping mechanism and are radially displaceable by means of a quick-acting clamping system. Eight hemispherical recesses and two clamping balls are preferably provided.

In the operationally ready state, a minimum play must remain between the recesses and the clamping balls which makes it possible for the worktool shaft to oscillate or swing in the described manner.

Accordingly, another object of the present invention is to provide a dental tool holder apparatus for holding an endodontic filing tool having a filing end for filing tooth material, and a shaft connected to the filing end, the apparatus comprising a tool holder housing, a drive sleeve mounted for rotation in the housing, the drive sleeve having a borehole therethrough for receiving the lower end of the filing tool shaft, the borehole having a constant diameter cross section along the axis of the tool shaft for engaging the tool shaft for rotation while permitting swinging movements of the tool shaft, clamping means connected to the housing for engaging an upper end of the tool shaft to axially hold the tool shaft to the tool holder housing while permitting swinging movement of the filing tool about the upper end of its shaft, and drive means engaged with the drive sleeve for rotating the drive sleeve in the housing.

A still further object of the present invention is to provide a dental tool holder apparatus which is simple in design, rugged in construction and economical to manufacture.

The various features of novelty which characterize the invention are pointed out with particularity in the claims annexed to and forming a part of this disclosure. For a better understanding of the invention, its operating advantages and specific objectives attained by its use, reference should be had to the drawings and descriptive matter in which there is illustrated and described the preferred embodiment of the invention.

BRIEF DESCRIPTION OF THE DRAWINGS

In the drawings:

FIG. 4 is a sectional view taken along IV—IV in FIG. 1;

FIG. 5 is a side elevational view of a filing tool with shaft and needle;

FIG. 6 is a sectional view through a filing tool along line VI—VI in FIG. 5; and FIG. 7 is a detail view taken at VII in FIG. 1 on an enlarged scale.

DESCRIPTION OF THE PREFERRED EMBODIMENT

Figure 1:
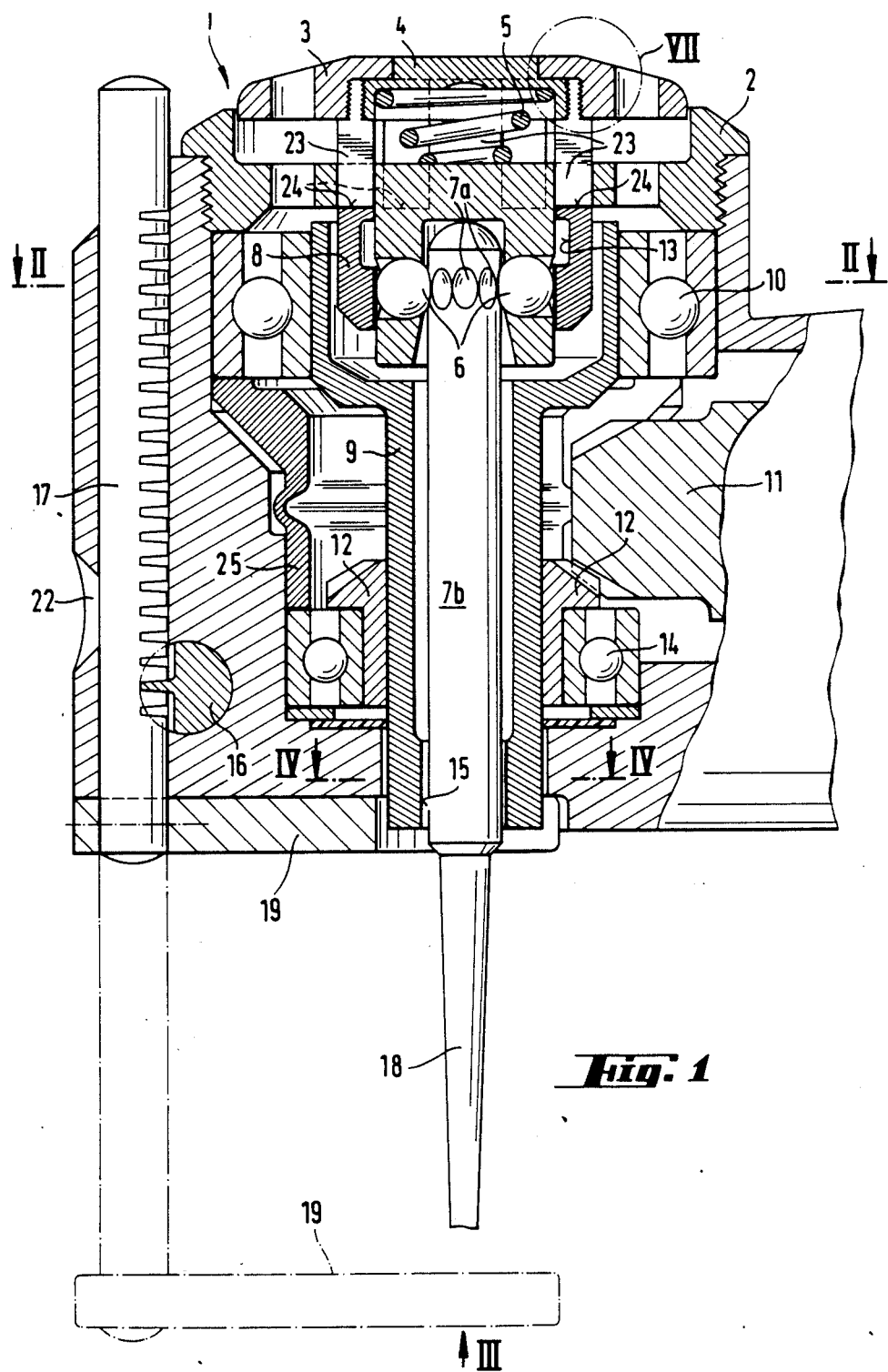
FIG. 1 is a longitudinal sectional view through the file angle head with inserted worktool.
Figure 2:
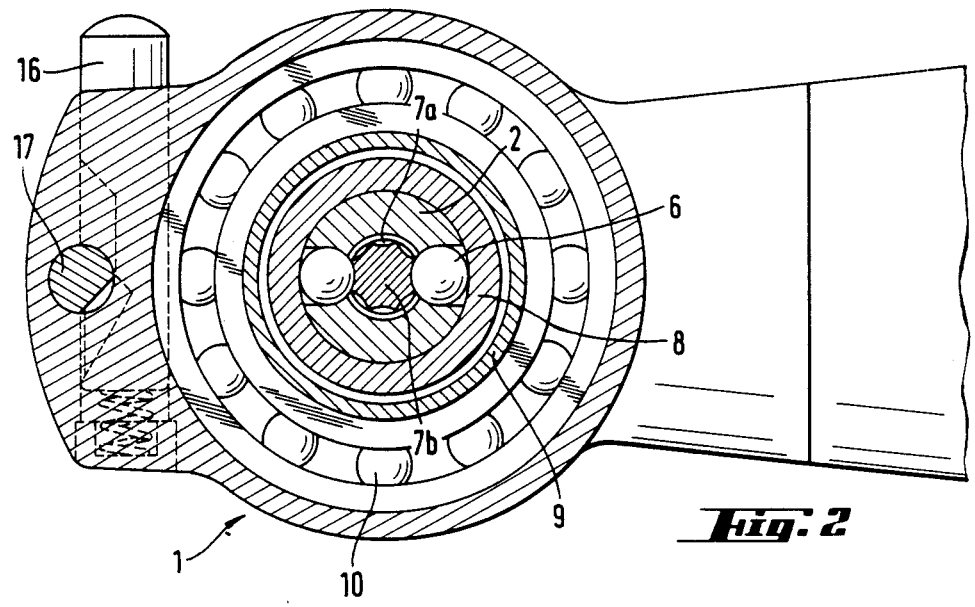
FIG. 2 is a sectional view taken along II—II in FIG. 1.

Referring now to the drawings, in particular the invention embodied in FIG. 1 comprises a handpiece or dental tool head generally designated 1 which carries a worktool holder 2.

The securely fitting work tool holder 2 is screwed into the head I of a dental angular tool holder or handpiece. A cylindrical clamping sleeve 8 projects through the worktool holder 2 with four webs 23 and is screwed to a two-part double-pressure cap 3, 4 (see FIG. 7). A conical pressure spring 5 forces the clamping mechanism 8, 4, 3 upwardly until cutout plane surfaces 24 of the clamping sleeve 8 abut at the worktool holder 2. In this clamping position, two clamping balls 6 are pressed radially inwardly into cuplike indentations 7a of a worktool shaft 7b by means of the sleeve 8 just far enough so that a minimum play remains so that the movability of the worktool shaft is ensured. Worktool 18 has a lower filing end and an upper shaft 7b.

If the cap 3, 4 is pressed downwardly, an annular groove 13 on the inside of the clamping sleeve 8 is lowered to the height of the clamping balls 6. Accordingly, the balls can move outwardly in the radial direction and release the shaft 7b.

The worktool can be clamped in any angular position by means of an arrangement of eight indentations 7a in the shaft 7b.

This clamping system which is securely connected to the tool holder is enclosed by a rotating drive sleeve 9 which comprises a cylindrical recess or borehole at the lower end, whose cross section has the shape of a constant-diameter configuration 15, as shown in FIG. 4. Configuration 15 has three substantially identical curved arc sections. There is a minimum of play between this constant-diameter configuration and the worktool shaft 7b, but this does not prevent contact between the shaft and the drive sleeve during rotation of the drive sleeve 9.

The vibrating movement impressed on the worktool is swinging and aleatory (irregularly contingent). Movement of the worktool in the direction of the file axis does not occur.

The drive sleeve 9 is supported in ball bearings 10, 14 which are axially fixed by means of the worktool holder 2 and a spacer 25. The sleeve 9 is driven by means of an angular drive consisting of toothed gears 11, 12.

Figure 3:
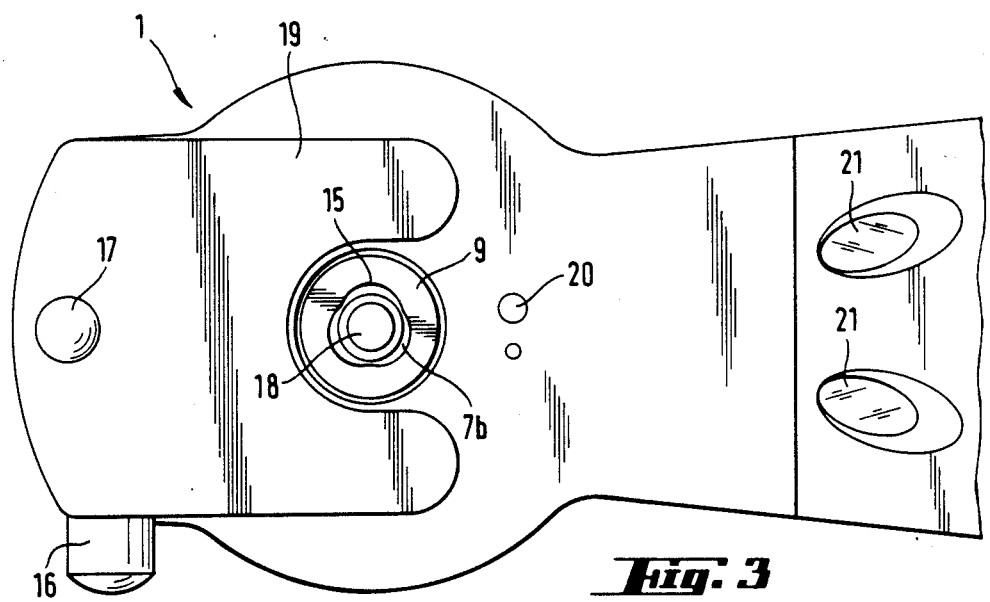
FIG. 3 is a view of the treatment head in the direction of arrow III in FIG. 1.

The maximum effective working length of the filing tool can be defined by means of a stop 19. The stop 19 is guided in the housing of handpiece 1 by means of a rod 17 which is fixed in the respective desired position by means of a crossbar 16. Bar 16 is spring-loaded to engage a tooth of rod 17. The rod 17 is provided with a scale which allows the respective depth position of the stop to be read at a cutout portion 22 of the head. Adjusting intervals of 0.5 mm preferably are provided. The stop 19 is advantageously constructed in such a way that it does not impede access of the cleaning and cooling fluid from the outlet point 20 to the worktool 18 and so that the tip of the filing tool 18 is sufficiently illuminated by means of two fiber optic light guide ends 21. To this end, stop 19 may be horseshoe shaped as shown in FIG. 3.

The invention is not limited to the embodiment which is shown. Thus, a different constant-diameter configuration can be selected, the clamping mechanism can be different and the depth stop need not be provided, or can have a different shape. It is also possible to construct the worktool shaft in the shape of a constant-diameter configuration and to construct the guide in a circular manner.

The support of the upper end of the worktool shaft with play and the excitement of the lower end of the worktool shaft by means of a constant-diameter configuration which rotates with play are substantial in the invention. If a three-sided constant-diameter configuration (trirondular configuration) is used, the rate of rotation of the constant-diameter configuration is preferably approximately 20,000 rpm which leads to a worktool frequency of approximately 1 kHz.

The mentioned tolerances and plays can be easily determined for the respective files and toolholders by a person skilled in the art with a knowledge of the invention. Likewise, the favorable rates of rotation for differently shaped constant-diameter configurations can be easily determined by a person skilled in the art with knowledge of the invention, possibly by means of simple experiments.

The cross section of the borehole 15 has a constant-diameter configuration taken in the axial direction of the tool shaft 7b while having an inner fluted or circumferentially and regularly variable contour. This shape causes engagement between the drive sleeve 9 and the tool 18 to rotate the tool 18 while, at the same time, permitting swinging pendulum-like movement of the drive tool about the upper end of shaft 7b. This produces the desired oscillations and movements of the lower filing end of the filing tool 18 which is supported by the shaft 7b of the tool.

While a specific embodiment of the invention has been shown and described in detail to illustrate the application of the inventive principles, it will be understood that the invention may be embodied otherwise without departing from such principles.

What is claimed is:

1. A dental toolholder apparatus in combination with and for holding an endodontic filing tool having a filing end for filing tooth material, and a shaft connected to the filing end, the apparatus comprising a toolholder housing, a drive sleeve mounted for rotation to said toolholder housing, said drive sleeve having a borehole therethrough for engaging a lower end of the tool shaft for rotating and oscillating the tool, said borehole having a cross section taken transversely to the axis of the filing tool which has a constant-drive configuration for rotating the tool while permitting swinging movement of the tool, clamping means connected to the housing for clamping an upper end of the tool shaft against axial movement to the housing while permitting swinging movement and rotation of the tool, and drive means operatively connected to said drive sleeve for rotating said drive sleeve.

2. An apparatus according to claim 1, wherein said clamping means includes at least one ball, at least one indentation in the upper end of the tool shaft for engagement by said at least one ball, a clamping sleeve movably mounted to said housing for radially engaging and holding said ball into said indentation and biasing means for biasing said clamping sleeve into a position engaging said ball into said indentation.

3. An apparatus according to claim 2, including a plurality of indentations circumferentially spaced around the upper end of the tool shaft and a plurality of said clamping balls each engageable into a respective one of said indentations.

4. An apparatus according to claim 3, including two clamping balls and eight indentations.

5. An apparatus according to claim 1, including stop means movably mounted to said housing and adjustment means for moving said stop means to extend down a selected length along the filing end to determine a length of the filing end exposed for filing tooth material.

6. An apparatus according to claim 5, wherein said stop means comprises a toothed rod mounted for movement to the housing parallel to the axis of the tool shaft, a stop fixed to said toothed rod and extendable along the length of the filing end of the tool with movement of the toothed rod, said adjusting means comprising a crossbar extending in said housing and engageable with a tooth of said toothed rod for holding said toothed rod at an axial fixed position in said housing, a spring engaged with said crossbar for holding said crossbar in engagement with the tooth of the toothed rod, said toothed rod having a scale thereon for indicating the position of said stop along the filing end of the tool, said housing having a cutout portion over said toothed rod for viewing said scale.

7. An apparatus according to claim 6, wherein the pitch of teeth in said toothed rod is about 0.5 mm, said rod being movable from 0 to 9 mm in said housing for controlling the depth of filing of tooth material by the filing end to the range between 0 and 9 mm.

8. An apparatus according to claim 6, including fluid feed means and illuminating means in said housing for supplying cooling fluid and illumination to the filing end of the tool, said fluid feed means comprising an outlet directed diagonally from said housing toward the filing end of the tool, said stop being in the form of a horseshoe and extending on a side of the filing end opposite from said outlet and said illuminating means.

9. An apparatus according to claim 1, wherein said borehole has a circumferentially regularly fluted inner surface.

10. An apparatus according to claim 9, wherein said fluted inner surface comprises three substantially identical curved arc segments.

* * * * *